(12) United States Patent
Imran et al.

(10) Patent No.: US 6,241,744 B1
(45) Date of Patent: Jun. 5, 2001

(54) APPARATUS FOR DEPLOYING A GUIDEWIRE ACROSS A COMPLEX LESION

(75) Inventors: Mir A. Imran, Los Altos Hills; Theodore C. Ormsby, Milpitas; Carole M. Sykes, Burlingame; Jeffrey S. Frisbie, San Jose; Kevin H. Van Bladel, San Mateo; Scott A. McGill, Redwood City, all of CA (US); Osamu Katoh, Kyoto (JP)

(73) Assignee: Fox Hollow Technologies, Inc., Redwood City, CA (US)

( * ) Notice: Subject to any disclaimer, the term of this patent is extended or adjusted under 35 U.S.C. 154(b) by 0 days.

(21) Appl. No.: 09/216,629

(22) Filed: Dec. 16, 1998

Related U.S. Application Data (63) Continuation-in-part of application No. 09/134,744, filed on Aug. 14, 1998.

(51) Int. Cl.[7] .................................................. A61B 17/22
(52) U.S. Cl. .......................... 606/159; 606/167; 128/898; 128/916; 600/585
(58) Field of Search .................................... 128/898, 916; 600/585, 434; 606/1, 159, 167, 170, 171, 185; 604/523, 528

(56) References Cited

U.S. PATENT DOCUMENTS

| | | |
|---|---|---|
| 5,000,185 | 3/1991 | Yock . |
| 5,029,588 | 7/1991 | Yock ................................. 128/662.06 |
| 5,120,323 | 6/1992 | Shockey et al. ...................... 604/282 |
| 5,127,917 | 7/1992 | Niederhauser et al. .............. 606/191 |
| 5,368,035 | 11/1994 | Hamm et al. . |
| 5,527,298 | 6/1996 | Vance et al. .......................... 604/280 |
| 5,531,700 | 7/1996 | Moore et al. ......................... 604/164 |
| 5,688,234 | 11/1997 | Frisbie .................................... 604/22 |
| 5,715,825 | 2/1998 | Crowley . |
| 5,775,327 | * 7/1998 | Randolph et al. .................... 600/434 |
| 6,036,646 | * 3/2000 | Barthe et al. ......................... 600/443 |

* cited by examiner

Primary Examiner—Glenn K. Dawson
(74) Attorney, Agent, or Firm—Townsend and Townsend and Crew LLP (57) ABSTRACT

An apparatus for deploying a guidewire across a complex lesion in a vessel formed by a wall and normally having a lumen extending therethrough including an elongate flexible catheter having proximal and distal extremities and having a plurality of separate spaced apart lumens therein extending from the proximal extremity into a location at least adjacent the distal extremity. A handle is mounted on the proximal extremity of the flexible elongate catheter. A flexible elongate sheath is mounted on the catheter and has a proximal portion, a transition portion and a distal portion with the transition portion being in the vicinity of the distal extremity of the catheter. The sheath has a lumen therein extending from the proximal portion through the transition portion and through the distal portion. First and second devices are slidably mounted in the spaced-apart lumens of said catheter. The lumen in the distal portion of said sheath has a size so that it can accommodate only one at a time of the at least two devices.

9 Claims, 8 Drawing Sheets

APPARATUS FOR DEPLOYING A GUIDEWIRE ACROSS A COMPLEX LESION

This application is a continuation-in-part of Application Ser. No. 09/134,744 filed Aug. 14, 1998, now pending.

This invention relates to an apparatus and method for deploying a guidewire across a complex lesion.

Apparatus of various types have heretofore been provided for advancing guidewires through lesions. However, where lesions are totally occluded or almost totally occluded, there is a great difficulty in crossing such stenoses. There is therefore a need for a new and improved method and apparatus for deploying a guidewire across a complex lesion.

In general, it is an object of the present invention to provide an apparatus and method for deploying a guidewire across a complex lesion.

Another object of the invention is to provide an apparatus and method of the above character which permits use of various devices without losing the position of a tip of a guidewire.

Another object of the invention is to provide an apparatus and method of the above character in which the physician can readily switch between different devices in a medical procedure.

Another object of the invention is to provide an apparatus and method of the above character in which a sheath is utilized for speed in negotiating a vessel.

Another object of the invention is to provide an apparatus and method of the above character in which it is possible to rotate the distal tip of the sheath without rotation of a multi-lumen catheter.

Another object of the invention is to provide an apparatus and method of the above character utilizing forward-locking ultrasound image guidance for negotiating passage through complex lesions in the coronary arteries.

Another object of the invention is to provide an apparatus and method of the above character in which the distal extremity of a catheter can be steered as it is advanced across a lesion.

Another object of the invention is to provide an apparatus and method of the above character in which the catheter is provided with a deflectable tip that permits primary (coarse) steering and has an ultrasound probe with a beveled tip surface that permits secondary (fine) steering during advancement of the tip through a lesion.

Additional objects and features of the invention will appear from the following description in which the preferred embodiments are set forth in detail in conjunction with the accompanying drawings.

In general the apparatus for deploying a guidewire across a complex lesion in a vessel formed by a wall and normally having a lumen extending therethrough is comprised of a flexible elongate catheter having proximal and distal extremities and having a plurality of spaced-apart lumens therein extending from the proximal extremity into a location at least adjacent to the distal extremity. A handle is mounted on the proximal extremity of the flexible elongate catheter. A flexible elongate sheath is mounted on the catheter and has a proximal portion, a transition portion and a distal portion with the transition portion being in the vicinity of the distal extremity of the catheter. The sheath has a lumen therein extending from the proximal portion through the transition portion and through the distal portion. First and second devices are slidably mounted in the spaced-apart lumens of the catheter. The lumen in the distal portion of the sheath has a size so that it can accommodate only one at a time of said at least two devices.

More particularly as shown in FIGS. 1 through 21, the apparatus 21 for deploying a guidewire across a complex lesion consists of a multi-lumen catheter 22 and an outer sheath 23. A plurality of devices at least one of which includes a guidewire such as three devices 24, 26 and 27 are deployable through the multi-lumen catheter 22 and the outer sheath 23. At least one of the devices 24, 26 and 27 as for example device 26 carries an ultrasonic transducer as hereinafter described and is connected by a cable 31 to a case 32 carrying electronics of the type hereinafter described and which has associated therewith a computer 33 of a suitable type as for example a laptop computer having a screen 34 as shown. The device 26 also can be identified as an ultrasonic probe or ultrasonic wire.

Figures 1, 2, 3:
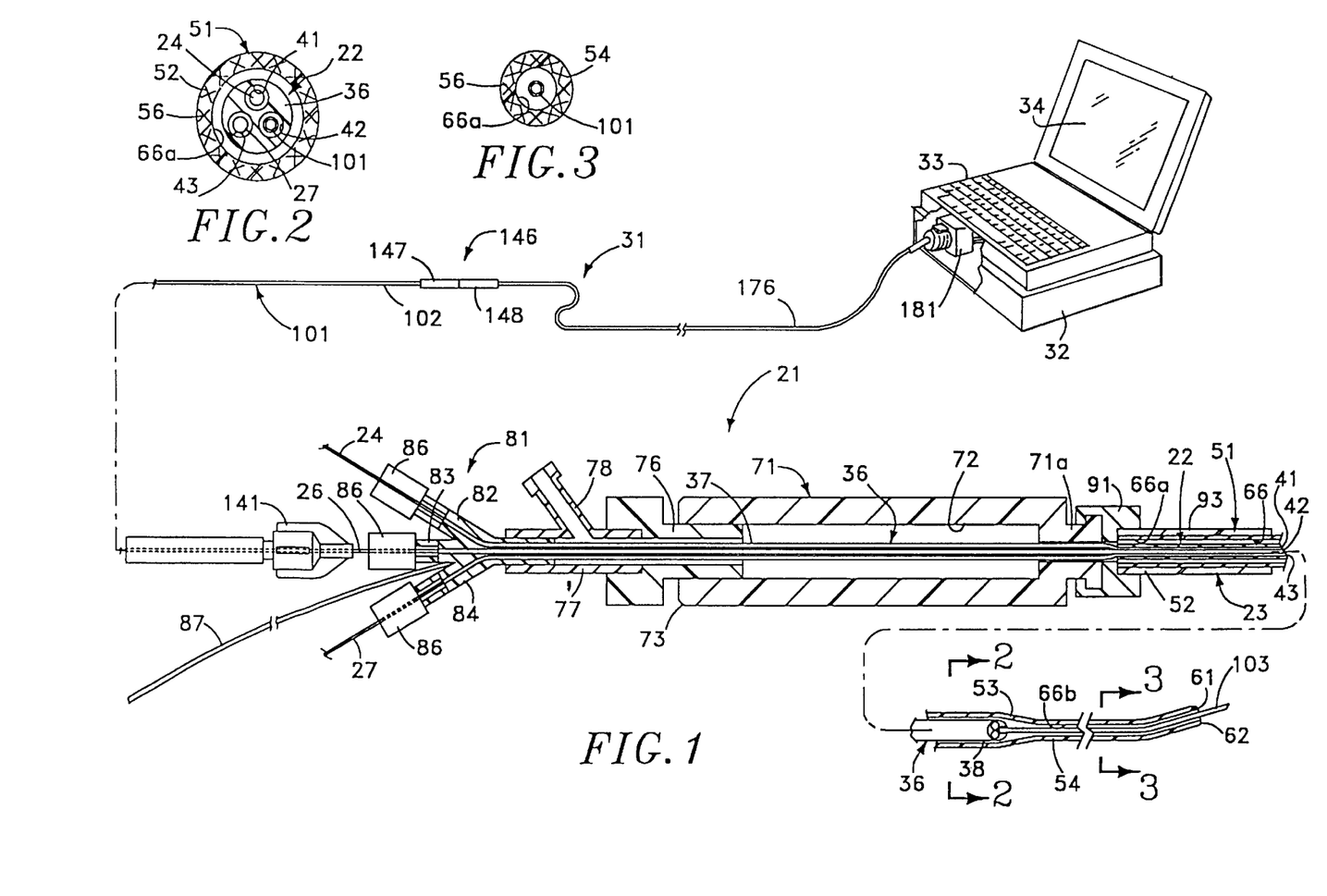
FIG. 1 is an isometric view of an apparatus for deploying a guidewire across a complex lesion showing the catheter and sheath in cross section.
FIG. 2 is an enlarged cross-sectional view taken along the line 2—2 of FIG. 1.
FIG. 3 is an enlarged cross-sectional view taken along the line 3—3 of FIG. 1.

The catheter 22 consists of a flexible elongate member 36 having proximal and distal extremities 37 and 38. The member 36 is formed of a body of a suitable plastic material such as Pebax, a polyurethane, polyethylene, Nylon, Teflon, a polyimide and silicone. Typically it is in the form of extruded tubing which is extruded with a plurality of lumens therein extending from the proximal extremity to the distal extremity. For example tri-lumen tubing formed of a suitable material such as Nylon can be extruded to provide three axially disposed lumens 41, 42 and 43 extending the length thereof of a suitable interior diameter as for example ranging from 0.009" to 0.030" and preferably approximately 0.017" permitting the use of devices such as guidewires and probes with diameters ranging from 0.007" to 0.028" and preferably approximately 0.014". The member 36 has a suitable length as for example approximately 110 cm. The remaining material within the member has a thickness ranging from 0.0005" to 0.009" and preferably approximately 0.0005". The material utilized for forming the flexible elongate member 36 in order to make it substantially radiopaque under X-ray can have incorporated therein a suitable radiopacifier agent such as barium sulfate or a bismuth compound.

Alternatively, the flexible elongate member 36 can be formed of three separate tubes as for example three 0.001" to 0.005" and preferably 0.0015" wall polyimide tubes having lumens therein of the dimensions hereinbefore described for the flexible elongate member 36. The tubes can be fastened together in a formation which is triangular in cross section and coated with a suitable bonding material such as a polyimide to provide a construction which can be utilized for the same purpose as the integral flexible elongate member 36 hereinbefore described.

The outer sheath 23 is also formed of a flexible elongate member 51 having a proximal portion 52, a transition portion 53 and a distal portion 54. The distal portion 54 has a length of approximately 20 cm and the transition portion has a suitable length as for example approximately 2 cm.

The flexible elongate member 51 is also formed of a plastic material such as Pebax, a polyurethane, polyethylene, Nylon, Teflon, a polyimide and silicone. In order to provide good torque transmission for reasons hereinafter explained, braid 56 in the form of cylindrical sleeve is incorporated into the material as it is extruded or alternatively, outer and inner liners can be utilized with the braid bonded therebetween. For example if Pebax is utilized, Pebax having a shore hardness of 72 D can be utilized to provide a braided tubular member 51. The braid 56 can be of a suitable type 0.0003" to 0.003"×0.001" to 0.005" and preferably 0.001"×0.003" stainless steel flat wire of 4–32 strands and preferably 16 strands, of 35–125 ppi and preferably 72 ppi. In order to provide the desired radiopacity, a radiopacifier agent such as barium sulfate or a bismuth compound can be incorporated into the material for the member 51. The proximal portion 52 of the member 51 can have a suitable size ranging in diameter from 0.052" to 0.079" and preferably approximately 0.065" corresponding to 5 French. The distal portion 54 has a smaller diameter than the proximal portion 52 and can have an outer diameter ranging from 0.014" to 0.038" and preferably 0.032". The distal portion also can have a braid 56 extending therethrough to provide torquability. It also can be provided with a radiopacifier agent to permit viewing of the same under X-ray.

Figures 4, 5, 7, 8:
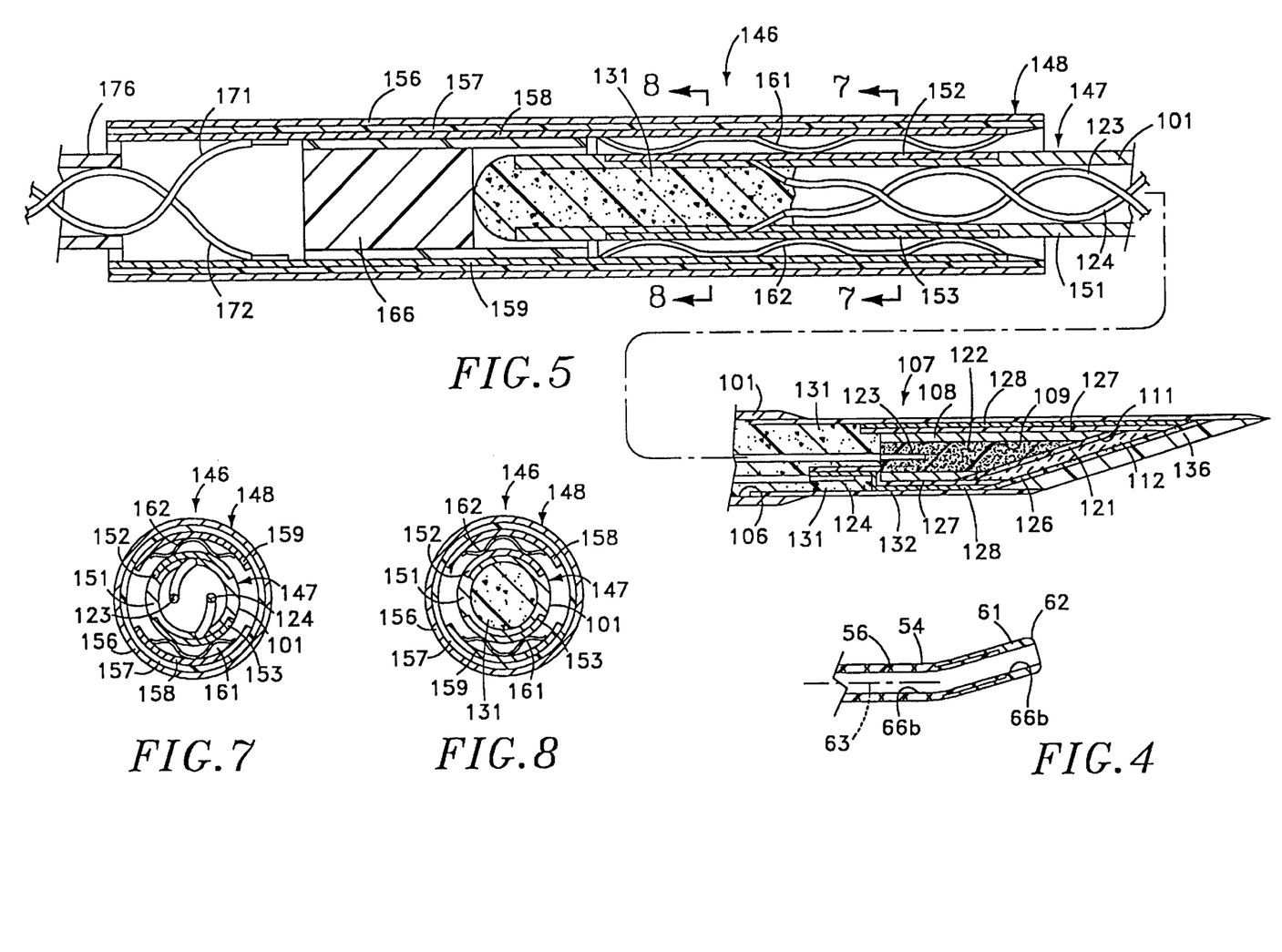
FIG. 4 is an enlarged view of the atraumatic tip of the sheath shown in FIG. 1.
FIG. 5 is an enlarged cross-sectional view of the connector 146 shown in FIG. 1.
FIG. 7 is a cross-sectional view taken along the line 7—7 of FIG. 5.
FIG. 8 is a cross-sectional view taken along the line 8—8 of FIG. 5.

An atraumatic tip 61 is provided on the distal extremity and is formed of a suitable material such as Pebax having a Shore hardness of 40 D. The tip 61 has a suitable length as for example 3 mm and is secured thereto in a suitable manner such as by a butt weld and a suitable adhesive. The front surface 62 of the atraumatic tip 61 can be rounded or beveled as shown to aid in preventing damage to the vessel wall when the apparatus is used as hereinafter described and also to provide a smooth transition from a guidewire or a probe which is introduced therethrough as hereinafter described. The atraumatic tip 61 is inclined upwardly at a suitable angle as for example 10–30° and preferably approximately 15° with respect to a longitudinal axis 63 of the distal portion 54 as shown in FIG. 4. Alternatively the tip 61 can be rounded.

The flexible elongate member 51 is provided with a lumen 66 extending therethrough with the portion 66a within the proximal portion 52 which may be but not necessarily of a larger diameter than the outside diameter of the proximal portion 37 of the flexible elongate member 36 through which a liquid such as a radiopaque agent can be introduced. The size of the lumen 66a also makes it possible to slidably and rotatably mount the outer sheath 23 on the catheter 22 for a purpose hereinafter described. The transition portion 53 of the flexible elongate member 51 is distal of the distal extremity of the catheter 22 and causes necking down of the lumen 66 so that it has a portion 66b of a smaller diameter which is sized to just accommodate any one of the devices 24, 26 and 27 carried by the catheter 22. The portion 66b can have an internal diameter ranging from 0.009" to 0.030" and preferably 0.017". This lumen portion 66b extends through the soft atraumatic tip 61.

The catheter 22 includes a handle 71 which is secured to the proximal extremity of the flexible elongate member 36. The handle 71 is formed of a suitable material such as a polycarbonate, ABS, or Delrin and can have a suitable length as for example 3" and an outside diameter of ½". The handle 71 if desired can be ergonomically designed. The handle is provided with a bore 72 of a suitable size as for example 0.250" through which the proximal extremity of the flexible elongate member 36 extends. The handle 71 is provided with a chamfer 73 on its proximal extremity. A fitting 76 is mounted in the bore 72 and has a Y-fitting 77 removably mounted thereon of which a side arm 78 serves to provide a flushing port for the introduction of certain liquids as for example a saline solution or alternatively a radiopaque agent. A connector 81 is removably mounted on the Y-fitting 77 and is provided with three legs 82, 83 and 84 which are in communication with the three lumens 41, 42 and 43 provided in the flexible elongate member 36. A hemostasis valve 86 is mounted on each of the three legs or arms 82, 83 and 84.

A length marker 87 is provided in the form of a flexible elongate element to ascertain the distance a device 24, 26 or 27 must be retracted to clear the lumen portion 66b. This element 87 can be formed of a plastic tube or a solid tubular member which is secured to the connector 81 by a suitable means such as an adhesive (not shown). The length of the element 87 is chosen to correspond to this distance.

A rotatable hub 91 is secured to the distal extremity of the handle 71 and is rotatable with respect thereto. The proximal portion of the flexible elongate member 51 of the outer sheath 23 is secured to the rotatable hub 91 so that if desired, the sheath 23 can be rotated independently of the multi-lumen catheter 22. A strain relief sleeve 93 extends forwardly from the rotatable hub 91 over the proximal extremity of the outer sheath 23.

Figure 6:
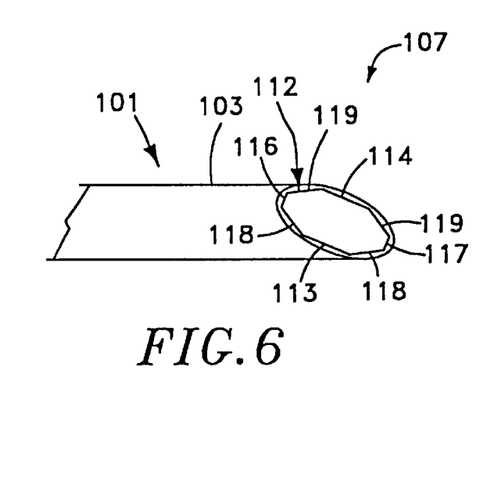
FIG. 6 is an isometric view showing the distal extremity of an ultrasonic probe incorporating the present invention.
Figure 9:
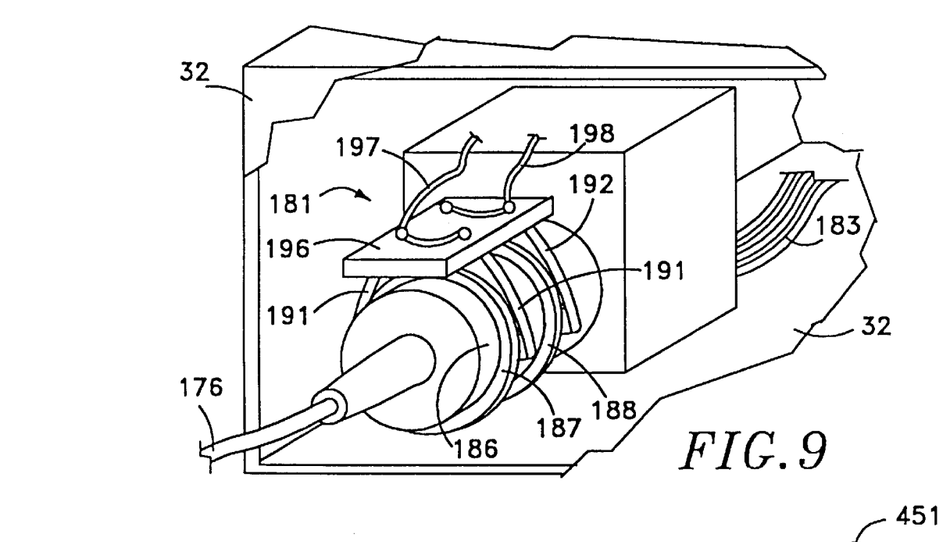
FIG. 9 is an enlarged isometric view of the shaft encoder shown in FIG. 1.

Let it be assumed that the device 26 is an ultrasonic probe in the form of a small diameter wire made in accordance with the present invention. This ultrasonic probe consists of a flexible elongate member 101 having proximal and distal extremities 102 and 103. The flexible elongate member 101 has a suitable length as for example 175 cm and can be formed of a biocompatible tubing of a suitable material as for example Nitinol or 304 stainless steel having an outside diameter ranging from 0.010" to 0.018". The tubing can have a suitable wall thickness as for example 0.002 to 0.003" to provide a bore 106 extending from the proximal extremity 102 to the distal extremity 103.

A transducer assembly 107 is mounted on the distal extremity 103. The transducer assembly 107 consists of a stainless steel tube 108 having a bore extending therethrough. The distal extremity of the tube 108 is provided with a bevel 111 which extends at an angle ranging from 10° to 80° with respect to the longitudinal axis of the tube 108. Preferably in accordance with the present invention, it is desired that this bevel extend in a direction so that the transducer mounted thereon as hereinafter described has forward looking capability as well as sideways looking capabilities.

A high efficiency piezoelectric transducer element 112 is provided which is sized so it is adapted to fit on the beveled surface 111. Because the area available for placement of the transducer element 112 is very small, it is desirable that the size of the transducer element be maximized as much as possible. Thus the transducer element is provided with an octagonal shape as shown in FIG. 6 having two long parallel spaced apart sides 113 and 114 and end sides 116 and 117 on each end at right angles thereto and adjoining sides 118 and 119 which are inclined at an angle with respect to the sides 113 and 114 on each end to provide the octagonal configuration. The transducer 112 is adhered to the beveled surface 111 by a layer of conductive adhesive 121 secured to the back side of the transducer 112 and secured to the beveled surface 111 of the tube 108. A silver epoxy 122 fills the bore 109 and makes contact with the conductive adhesive 121 and has embedded therein a conductor 123 of a twisted pair of insulated conductors 123 and 124 which extend through the bore 106 of the flexible elongate tubular member or hypotube 101. A conductive adhesive layer 126 is also provided on the front surface of the transducer element 112. A layer 127 of insulating material overlies the outer surface of the tube 108. A layer 128 of a suitable conductive material such as silver, gold or platinum is placed over the insulating layer and makes contact with the conductive adhesive layer 126 to thereby provide contact between the front surface of the transducer and the conductor 124 of the twisted pair. An insulating epoxy 131 is provided in the space just proximal of the tube 108 and extends into the distal extremity of the bore 106 of the hypotube 101 to support the twisted pair of conductors and also to support the transducer assembly 107. An insulating layer 132 overlies the epoxy 131 and the conductive layer 128. An acoustic matching layer 136 formed of a suitable material such as Tracon 3101 is provided over the thin conductive adhesive layer 126.

A pin-vise or torquer 141 is mounted on the proximal extremity 102 of the flexible elongate member 101 and is provided for manually rotating the ultrasonic probe 26 as hereinafter described. A mechanical electrical connector assembly 146 is provided on the proximal extremity of the flexible elongate member 101 and is provided to serve as a sterile interface for a purpose hereinafter described. The connector assembly 146 (see FIGS. 5, 7 and 8) consists of male and female parts 147 and 148 respectively. The proximal extremity of the ultrasonic probe device has the male part 147 formed thereon. An insulating layer 151 is formed on the proximal extremity 102 of the flexible elongate member 101. Two spaced-apart half shells 152 and 153 formed of a suitable conductive material such as silver are secured to the insulating layer 151 but are spaced apart thereon to which electrical contact is made respectively by conductors 123 and 124.

The female part 148 consists of a metal sleeve 156 which has mounted therein an insulating sleeve 157 which overlie two spaced apart half shells 158 and 159 that carry spring fingers 161 and 162 that are adapted to be engaged and yieldably pushed outwardly by the male part 147 when it is introduced therein. A plug 166 is mounted in the connector assembly and limits the amount by which the male part 147 can penetrate into the female part 148 and to help ensure that the appropriate electrical connections are made. The half shells 158 and 159 are connected to another twisted pair of insulated conductors 171 and 172 and extend through another flexible elongate cable 176 (see FIGS. 1 and 5) which is capable of carrying the conductors 171 and 172 and is also capable of transmitting rotation mechanically on a one-to-one relationship as the ultrasonic probe is rotated. As shown in FIG. 1, cable 176 is connected into the cabinet or case 32 and is mounted therein as shown in a partial view in FIG. 9. The assembly 181 includes an angular encoder 182 of a conventional type which converts rotational information into a digital format which is supplied by a wiring 183 to a parallel port in a digital signal processor in circuitry provided within the case 32. The shaft (not shown) of the digital encoder is directly connected to a rotor 186 as shown which carries typically at least two insulated slip rings 187 and 188 which are engaged by spring fingers 191 and 192 carried by a stator block 196. The slip rings 187 and 188 are connected electrically to conductors 197 and 198 which are connected into the transmit/receive RF circuitry within the case 32.

Figures 10, 11, 12, 13:
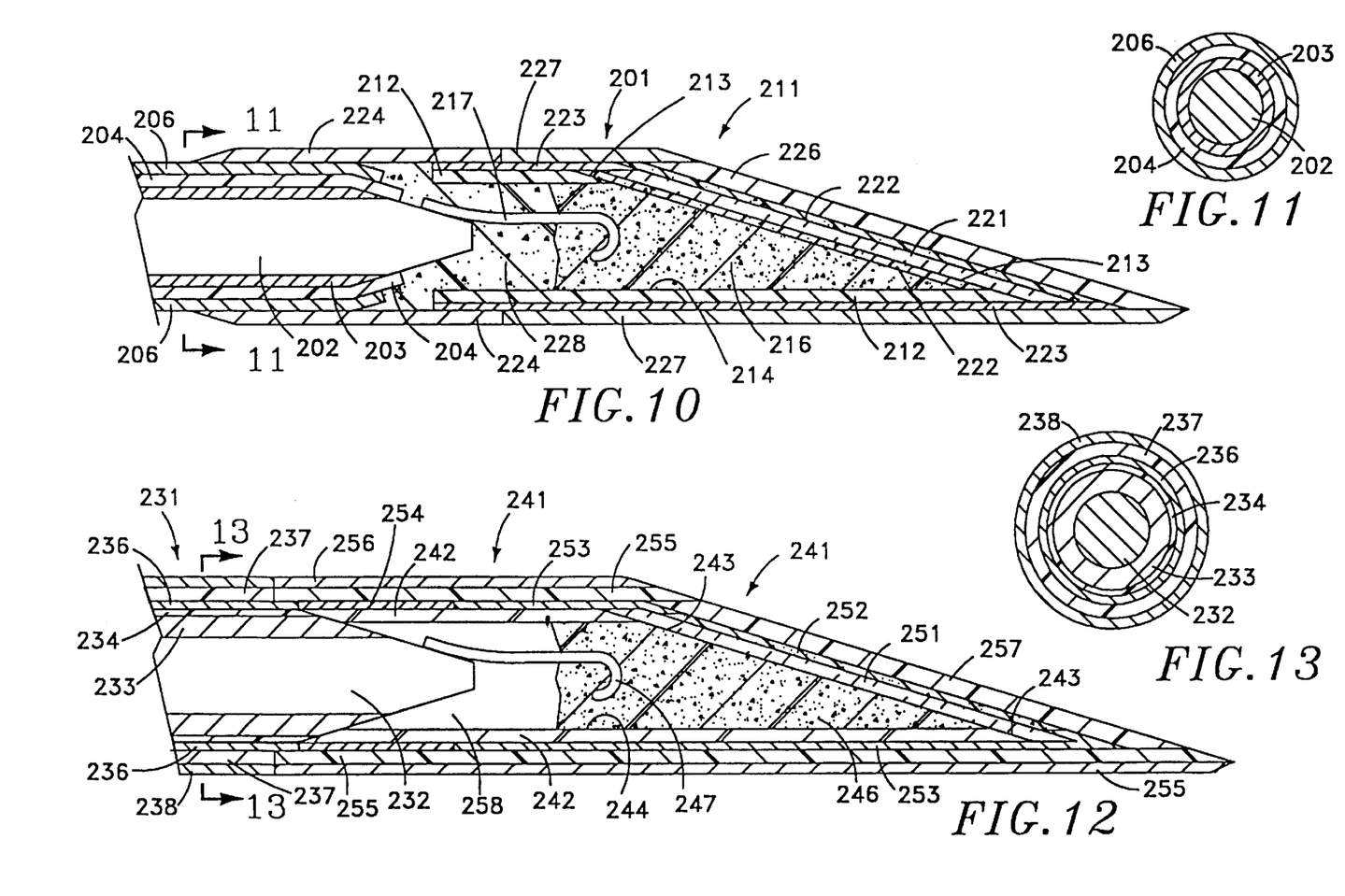
FIG. 10 is an enlarged cross-sectional view of the distal extremity of another embodiment of an ultrasonic probe incorporating the present invention.
FIG. 11 is a cross-sectional view taken along the line 11—11 of FIG. 10.
FIG. 12 is an enlarged cross-sectional view of another embodiment of an ultrasonic probe incorporating the present invention.
FIG. 13 is a cross-sectional view taken along the line 13—13 of FIG. 12.

Rather than providing a hollow tube for the flexible elongate member 101, a solid flexible elongate member 201 has been provided in the alternative embodiment shown in FIGS. 10 and 11. As shown therein, the flexible elongate member consists of a solid core 202 of a suitable conductive material such as silver which is covered with a layer 203 of a nickel-titanium alloy in which a distal extremity has been ground to expose the conductive core 202 as shown particularly in FIG. 10 at 202a. The nickel-titanium layer 203 is covered with a layer of insulation 204 which is covered by a layer 206 of a suitable conductive material such as silver.

A transducer assembly 211 similar to the transducer assembly 107 is mounted on the distal extremity of the flexible elongate member 201. The transducer assembly 211 consists of an insulating sleeve 212 which is provided with a tapering or inclined surface 213 that is inclined at an angle of from 10–80° with respect to the longitudinal axis of the insulating sleeve 212. The sleeve 212 is provided with a bore 214 which is filled with a silver epoxy 216. One end of a conductor 217 is embedded in the silver epoxy 216 and the other end of which is bonded to the exposed portion 202a of the conductive core 202 to form electrical contact therewith.

A transducer 221 of the type hereinbefore described is secured to the inclined surface 213 with a conductive adhesive 222 with its back surface in contact with the silver epoxy 216. A layer of conductive adhesive 222 is also provided on the front surface of the transducer 221 and is in electrical butt contact with a layer or coating 223 of a suitable material such as gold provided on the exterior surface of the insulating tube 212. This gold layer 223 makes contact with another tube 224 formed of a suitable conductive material such as silver which is in contact with the silver layer 206 as shown. It can be seen that conductors have been provided in the flexible elongate member 201 which are in contact with the front and back surfaces of the transducer 221. An impedance matching layer 226 overlies the conductive adhesive layer 222 and is disposed within the tapered distal extremity of an insulating tube 227 which overlies the gold coating 223. The silver epoxy 216 fills the voids or space within the tube 212 and serves to secure the transducer assembly 211 to the distal extremity of the flexible elongate member 201.

From the foregoing it can be seen that there has been provided a flexible elongate member 201 which has a solid construction which provides additional torque capabilities so as to provide substantially one-to-one correspondence between rotation of the distal extremity with respect to rotation of the proximal extremity. The use of the nickel-titanium alloy also provides additional flexibility without danger of kinking.

Still another embodiment of an ultrasonic probe incorporating the present invention is shown in the flexible elongate member 231 as shown in FIGS. 12 and 13. It consists of a center conductive core 232 formed of a suitable material such as silver which is covered by a sleeve 233 of a nickel-titanium alloy which has its distal extremity ground as shown to provide a silver core which is exposed as shown in FIG. 12. The nickel-titanium layer 233 is covered by a layer 234 of insulation. This insulation layer 234 is covered by a layer 236 of a conductive material. This layer of conductive material 236 is covered by a layer of insulation 237 and this layer is covered by a layer 238 of conductive material of a suitable type such as silver. From this construction it can be seen that there are provided three conductive elements in the flexible elongate member 231. A transducer assembly 241 is mounted on the distal extremity and consists of an insulating tube 242 which is provided with a tapered inclined surface 243 on its distal extremity which is provided with a bore 244 which is filled with a silver conductive epoxy 246 and which has embedded therein one end of a conductor 247 the other end of which is bonded by suitable means such as solder (not shown) to the silver core 232.

A transducer 251 of the type hereinbefore described is mounted on the inclined surface 243 and has its back side in contact with the conductive epoxy 246. The front side of the transducer 251 is coated with a layer 252 of a conductive adhesive which is in contact with a layer 253 of a suitable material such as gold or silver which makes a butt contact with a silver sleeve 254 that makes a butt contact with conducting layer 236. An insulating layer 255 overlies the layer 253 and adjoins insulating layer 237. A conductive layer 256 overlies the insulating layer 254 and is formed of a suitable material such as silver and adjoins the silver layer 238. An impedance matching layer 257 overlies the adhesive layer 252. In this embodiment of the flexible elongate member 231 it can be seen that there is provided an outer silver layer 238 which can serve as a signal ground. An epoxy 258 fills the space in bore 244 between the distal extremity of the silver core 232 and the silver epoxy 246.

In all of the foregoing constructions of the transducer assemblies, the transducer is insulated about its edges and coated with a thin conductive material extending to all proximal and distal surfaces. The first of these makes the connection to the back of the transducer and the second makes the connection to the front of the transducer. The impedance matching material for layers 226 and 257 is shaped to provide an impedance match and to optimize transducer performance in a biological environment such as in tissue and blood.

The probe device 21 is constructed in such a manner as to facilitate rotation of the same by the conventional pin-vise or torquer 141 secured to the proximal extremity so that it can be manually rotated to provide forward looking conically scanned images about the longitudinal axis of the probe device 21. The transducers will typically be operated in the 10–100 MHz range and preferably within 36 MHz to 90 MHz and with a mounting angle between 10–80° with respect to the probe's longitudinal axis and will have an aspect ratio range of 1:6 to 1:1.015. The beveled tips provided on the ultrasonic probes makes it possible for them to penetrate biological tissue when it is necessary to navigate a total occlusion or a near total occlusion.

Figure 14:
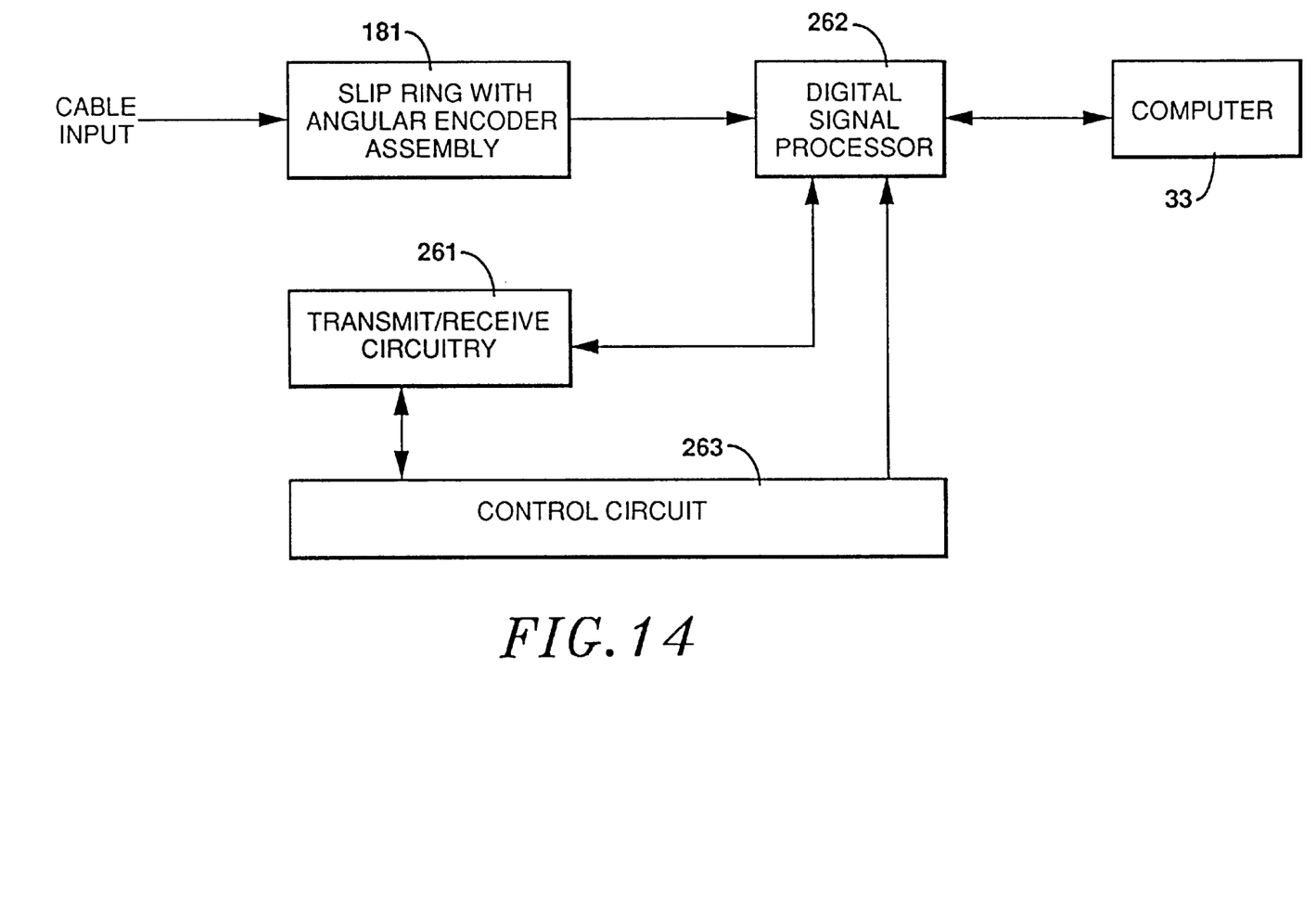
FIG. 14 is a block diagram of the electronic circuitry utilized in the apparatus shown in FIG. 1.

The apparatus 21 includes the circuitry which is shown in block diagram form in FIG. 14 within the case or cabinet 32 underlying the computer 33. As shown therein it includes the slip ring with angular encoder assembly 181 which receives its input from the cable 176. This assembly 181 receives the transmit and receive information from the transmit and receive circuitry 261 of a conventional type which can operate at a suitable analog radio frequency as for example 40 MHz which is supplied to and received from the transducer. Information received by the transmit and receive circuitry 261 and from the angular encoder of the assembly 181 is supplied to a digital signal processor 262 under the control of a control circuit 263. The output from the digital signal processor is supplied to the computer 33 which performs the necessary computational functions and supplies the results to the screen 34 which can be viewed by the physician performing the procedure.

Figure 15:
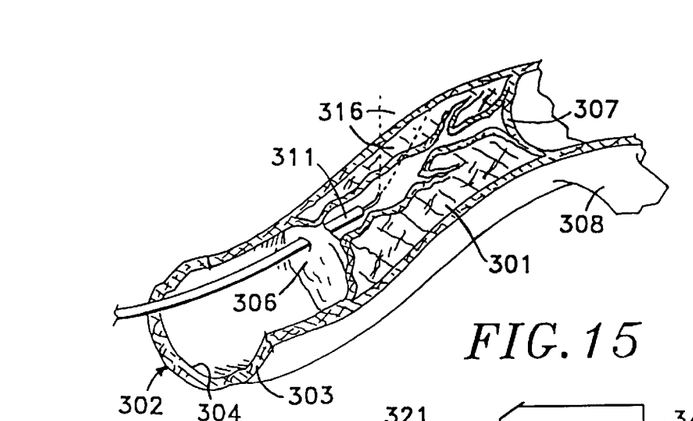
FIG. 15 is a cross-sectional view of a vessel having a complex lesion therein showing the method of the present invention utilizing the apparatus of the present invention for deploying a guidewire across a complex lesion.

Now let it be assumed that it is desired to utilize the apparatus 21 for deploying a guidewire across a complex lesion as for example such as a complex lesion 301 as shown in FIG. 15 which is disposed in a vessel 302 formed by a wall 303 and having a lumen 304 extending therethrough through which blood normally flows. This lumen 304 has been totally or partially occluded by a complex lesion or stenosis 301 which typically may have proximal and distal fibrous end caps 306 and 307 respectively. As shown, the vessel 302 can have a branch 308 extending just distally of the distal end cap 307.

Let it be assumed that it is desired to deploy a guidewire across this complex lesion or stenosis 301 and that is of a type which cannot be traversed by a conventional guidewire. The physician prepares the apparatus 21 for use by introducing for the second device 26 an ultrasonic probe of the type hereinbefore described in the lumen 41, a conventional stiff guidewire for the first device 24 in the lumen 42 and a conventional floppy type guidewire for the third device 27 in the lumen 43. They are all positioned so that their distal extremities are within the distal extremity of the catheter 22 and do not protrude therefrom. By way of example the femoral artery of the patient can be accessed in a conventional manner and a guiding catheter inserted therein and advanced until it is in an appropriate location. Thereafter with the devices 24, 26 and 27 having their distal extremities retracted into the distal extremity 38 of the catheter 22, the catheter 22 is advanced into the guiding sheath by first inserting the distal extremity of the outer sheath 23, pushing it into the guiding catheter utilizing the handle 71 while grasping it with one hand. Advancement can be continued rapidly without the use of the ultrasonic probe through the guiding catheter and thence into the lumen of interest. If it is desired to visualize the occlusion at this time, a radiopaque contrast medium can be introduced through the port 78 and passed through the lumen 66 and into the outer sheath 23 to fill the space immediately proximal to the lesion of the occluded vessel. Alternatively, the radiopaque contrast medium can be introduced through one of available lumens of the multi-lumen catheter 22. If some contrast medium appears beyond the distal part of the occlusion, this is an indication that a portion of the tissue on the other side of the lesion has been at least partially pressurized by collateral flow and is viable and salvageable. If the lesion forms a total occlusion, typically the radio contrast medium will not pass therethrough.

At this point in the procedure, it is desirable to utilize the ultrasonic probe that already has been connected to the computer 33. Since the other two devices 24 and 27 are retracted within the catheter 22, the ultrasonic probe 26 can be advanced into the lumen portion 66b so that its distal extremity extends out of the lumen and is disposed within the lumen 304 of the vessel 302. Radio frequency energy applied to the ultrasonic transducer causes ultrasound to be emitted therefrom in a beam which diverges slightly and depending upon the inclination of the transducer impinges on the inner surface of the wall and thereby provides an image of the wall of the vessel on the screen 34 of the computer 33. To obtain an image of a cross-section of the vessel, the transducer is rotated slowly by the physician using one hand to rotate the pin-vise through a couple of rotations to obtain a good image of the vessel and also to ascertain the location of the ultrasonic probe in the vessel. To achieve the desired orientation for the distal extremity of the ultrasonic probe, the physician can rotate the rotatable hub 91 to shift its angular position and thereby direct the angle of advancement of the distal extremity of the ultrasonic probe. Thus a physician by rotating the ultrasonic probe with the pin-vise 141 and by rotation of the outer sheath 23 by rotatable hub 91 can carefully guide the ultrasonic probe or wire 26 in the vessel without danger of penetrating the vessel wall and thereby advance it into an appropriate location adjacent the proximal end cap 306 of the lesion or stenosis 301.

During the time that the pin-vise 141 is being rotated, this rotation of the ultrasonic probe is tracked by the angle encoder 182 to supply that information to the electronic circuitry so that it can be utilized for the display on the screen 34. By use of the rotatable hub 91 it is possible to rotate the outer sheath 23 independently of rotation of the catheter 22 and the ultrasonic probe or wire 26.

In this manner it is possible for the physician to locate the best region in which to penetrate the proximal end cap 306. As soon as this has been ascertained, the handle 71 can be pushed forwardly to advance the outer sheath 23 so that the atraumatic tip 61 can follow the beveled and sharpened tip 111 of the transducer assembly 107. The distal extremity of the outer sheath 23 provides additional rigidity to the sharpened tip 111 to make it possible to penetrate relatively fibrous end caps. As soon as the proximal end cap 306 has been penetrated, the outer sheath 23 along with the ultrasonic probe or wire 26 is advanced into a fissure 311 within the stenosis 301. The physician by visualizing on the screen 34 the information obtained by the beam 316 as the ultrasonic probe or wire 26 is rotated and advanced through the stenosis along with the outer sheath 23. The outer sheath 23 may be independently rotated as needed to redirect the probe or wire 26 during advancement of the ultrasonic probe or wire 26 and the outer sheath 23 through the stenosis. The physician during this time is also observing fluoroscopically the advancement to find the most desirable passageway through the stenosis 301 and to find the most advantageous region to penetrate the distal end cap 307. Thereafter by advancement of the ultrasonic probe followed by advancement of the outer sheath 23, the ultrasonic probe or wire 26 and the sheath can be advanced through the distal end cap 307.

Thus it can be seen that the ultrasound images provided on the screen 34 provide necessary information to stay within the boundaries defined by the vessel wall 303. The use of the ultrasonic probe also makes it possible to avoid hard calcified lesions which would be impossible or difficult to break through. Using the apparatus of the present invention, there is a much greater likelihood of finding the original lumen that was closed up by the thrombus creating the lesion or stenosis. The ultrasonic probe will also make it possible to locate softer deposited material which can be more easily penetrated. After the ultrasound probe has penetrated the distal end cap 307, it can be utilized to detect the flow of blood on the other side of the occlusion and determine whether the flow is in the main branch or in a side branch. After this has been determined and it is no longer necessary to utilize the ultrasonic probe, the ultrasonic probe is withdrawn over a suitable length as for example the length of the length marker 87 to ensure that the distal extremity of the ultrasonic probe has been withdrawn into the distal extremity of the catheter 22. If desired, radiopaque contrast medium can then be introduced through the port 78 to permit viewing of the vessel distally of the stenosis or lesion 301. Alternatively, the physician can select one of the devices 24 and 27, either a stiffer guidewire or a floppy tip guidewire, and advance the same through the outer sheath 23 so that it extends beyond the stenosis or lesion which it has been desired to traverse. After the guidewire is positioned so that its distal extremity is beyond the lesion 301, the outer sheath 23 and the catheter 22 with the ultrasonic probe 24 therein and the other guidewire therein can be removed, leaving the deployed guidewire in place.

With the guidewire in place extending beyond the stenosis, the guidewire can be utilized in a conventional manner for delivering other medical devices as for example a balloon catheter over the guidewire until the balloon is in registration with the stenosis, after which the balloon can be inflated to compress the stenosis and to provide a larger opening through the stenosis. As is well known to those skilled in the art, one or more balloon catheters can be utilized in this procedure. In addition, a stent can be deployed which can be either a balloon expandable stent or a self-expanding stent that is delivered into the stenosis and left in place, after which the stent placement balloon catheter and the guidewire can be removed. The opening in the femoral artery can then be closed in a conventional manner.

After the procedure has been completed, the portion of the apparatus extending proximally from the connector assembly 146 can be separated at the connector 146 with the cable 176, the case 32 and the computer 33 being saved because they are used outside of the sterile field. The remainder of the apparatus operates in the sterile field and is typically disposed of after use.

From the foregoing it can be seen that there has been provided an apparatus and method which makes it possible by the use of ultrasonics to navigate through near if not at the center of a vessel without danger of perforating the wall of the vessel while at the same time finding the most efficacious route to traverse a stenosis or lesion in the vessel so that a guidewire can be delivered safely and efficiently through the stenosis. A quick disconnect is provided for separating the portions of the apparatus which are deployed in the sterile field and those portions which are not. The beveled tip provided on the ultrasound probe makes it possible to look forwardly at the same time that sideways looking is taking place to facilitate navigation of the lumen in the vessel.

The display screen 34 during use will typically display side by side two circular images, one a real time image 321 (see FIG. 16) and the other an archived image 322 as for example an accumulation of a plurality of several real time images typically from 10–50 deep. The display 34 also can be utilized for displaying other menu-activated items such as time, date, patient name, comments, etc. By providing multiple devices in the catheter, it is possible to make a rapid exchange between devices without the necessity of removing the catheter from the patient.

By way of example, the real time image 321 (see FIG. 16) shows an angular vector 326 which is positioned at an angle corresponding to the angle at which the transducer 251 is pointing in the lesion 301. As shown in the real time image 321, this single vector 326 is typically rotated in a plane perpendicular to the longitudinal axis of the forward looking transducer 251 through 360° to provide a composite of multiple vectors to provide a forward looking conical image. As shown the real time image displays the position of the distal extremity 103 of the flexible elongate member 101 with respect to the wall 303 and with respect to calcification 328 appearing in the lesion or stenosis 301 within the wall 303. Thus it can be seen that the real time image 321 displayed indicates that it would be desirable to move the distal extremity 103 in a direction away from the wall 303 towards the center of the vessel 302 so that it is centered within the vessel 302 such as in the archived image 322. Thus as the physician or surgeon rotates the beveled surface 111 of the ultrasonic guidewire device 26, the angular vector 326 will move with it so that the physician by viewing the screen 34 can ascertain the position of the beveled surface 111 and thereby gauge the positioning of the beveled surface within the vessel with respect to the walls of the vessel and any calcification contained therein. Thus typically to move away from a wall, the outer sheath 23 may be rotated through 180° or the probe or wire 26 may be rotated so that its beveled face faces the wall and is then advanced to move the probe or wire 26 away from the wall. It is preferable to be as close to the center of the vessel as possible to minimize any chance of perforating the wall of the vessel with the sharpened beveled tip. It also should be appreciated that it is desirable to penetrate the lesion through the softest tissue area which may not necessarily be in the exact center of the wall for the vessel.

Figures 16, 24:
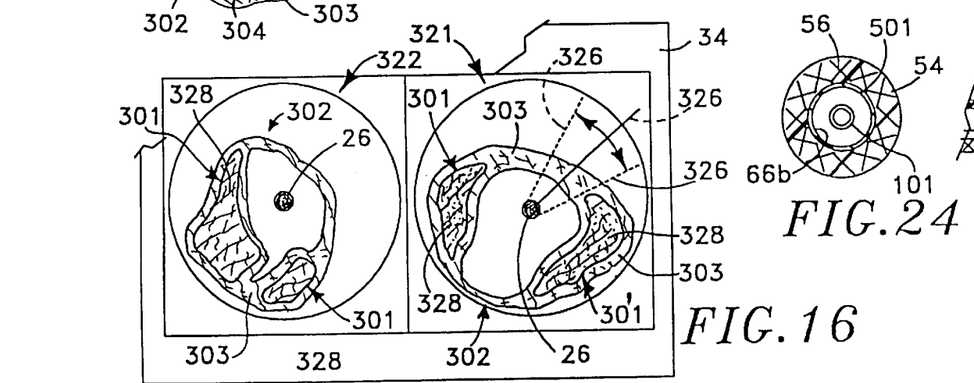
FIG. 16 is an illustration showing juxtaposed archived and real time images on the screen of the computer illustrating deployment of the guidewire as in FIG. 15.
FIG. 24 is a cross sectional view taken along the line 24—24 of FIG. 23.

During the time that this advancement is being placed, archived images are being stored to provide a reference for the regions being traversed so that if desired, the physician can pull back the ultrasonic probe 26 and then use the archived information to traverse along the same path as previously selected. From the foregoing it can be seen that the screen 34 depicts an angular vector 326 which corresponds to the exact polar angles of the beveled transducer surface. Thus this makes it possible for the physician to maneuver away from the wall of the vessel and at the same time to maneuver around calcified deposits in the vessel.

Thus it can be seen that the ultrasonic guidance system which utilizes a rotatable outer sheath and a forward looking ultrasound imaging guidewire in connection with the electronics hereinbefore described makes it possible to display scan converted ultrasound echo vectors. The ultrasound echo signal is combined with the angular position from the encoder to produce a vector on the display. As the ultrasound guidewire is rotated on its longitudinal axis, a set of vectors are created, processed and displayed to aid physicians in navigating the ultrasound guidewire through an occlusion. The displayed image is a two-dimensional compressed image of a three-dimensional conical surface generated as a result of rotating the ultrasound transducer on its axis about 360° with its beveled surface being disposed at an angle ranging between 10° and 80°. The image field closest to the center is least forward and the image field farthest from the center is more forward with respect to the transducer located at the guidewire tip.

In order to provide additional lubricity within the lumens hereinbefore described in the apparatus, the lumens can be lined with a lubricious material as for example PTFE.

Figures 17, 18, 19, 20, 21:
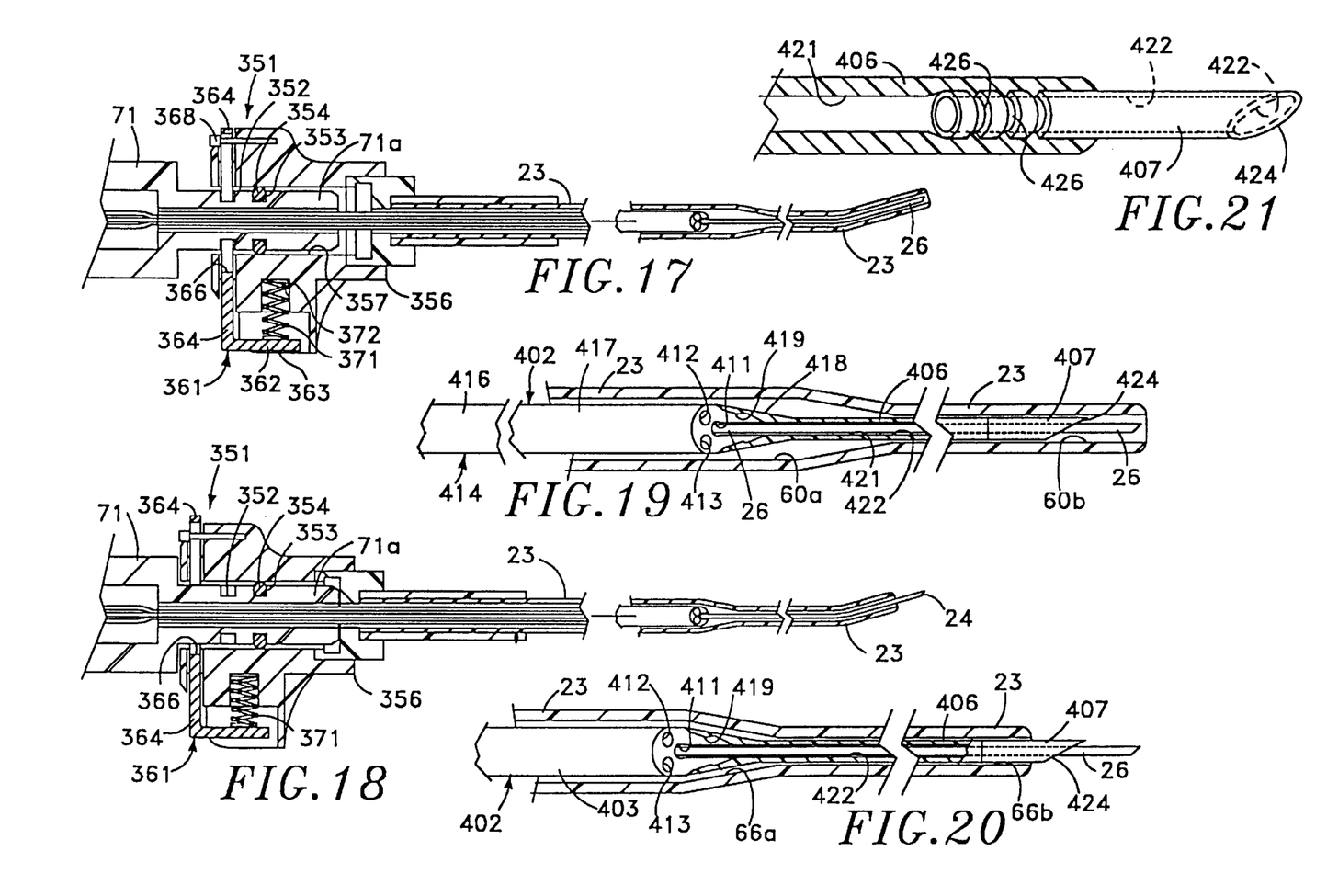
FIG. 17 is a side elevational view partially in cross section of another apparatus incorporating the present invention showing the detent mechanism in an advanced position.
FIG. 18 is a view similar to FIG. 17 but showing the detent mechanism in a retracted position.
FIG. 19 is a partial side elevational view of another embodiment of an apparatus incorporating the present invention utilizing a modified catheter shown in a retracted position within the sheath.
FIG. 20 is a cross-sectional view similar to FIG. 19 but showing the catheter in an advanced position with respect to the sheath.
FIG. 21 is an enlarged side elevational view of the cannula tip shown in FIGS. 19 and 20.

Another embodiment of the apparatus incorporated in the present invention is shown in the apparatus 351 in FIGS. 17 and 18. As shown therein, the handle 71 has been provided with a cylindrical extension 71a which is provided with an annular recess 352 just distal of the handle 71. Another annular recess 353 is provided distally of the annular recess 352 and has disposed therein an O-ring 354 which forms a sealing engagement with the rotatable hub 356 that is provided with a bore 357 of a slightly larger diameter than the cylindrical extension 71a to permit slidable and rotational movement of the rotatable hub 356 with respect to the cylindrical extension 71a.

Locking means is provided for permitting longitudinal or axial movement of the rotatable hub 356 with respect to the cylindrical extension 71a and consists of a detent mechanism 361 including a tab 362 which is adapted to be engaged by a finger of the same hand holding the handle 71 as for example the thumb. The tab 362 is formed integrally with a slider 363 mounted in a slot 364. The slider is provided with a circular opening 366 through which the cylindrical extension 71a extends. The slider 363 is also provided with a slot 367 which opens into the circular opening 366 at the top thereof. A pin 368 extends into the hub 356 through the slot 367 and permits movement of the slider 363 between recess engaging and recess disengaging positions against the force of a spring 371 mounted in a well 372 on the rotatable hub 356. Thus it can be seen as shown in FIG. 17 when the slider 364 is in engagement with the slot 352, the outer sheath extends over the end of the ultrasonic probe so that the device 26 therein has its distal extremity retracted within the distal extremity of the outer sheath 23. When it is desired to advance the distal extremity of the device 26 out of the outer sheath 23, this can be accomplished by depressing the tab 362 and pulling the rotatable hub 356 proximally until the rotatable hub abuts the handle 71 which at the same time causes the distal extremity of the device 26 to extend beyond the distal extremity of the outer sheath as shown in FIG. 18. Thus it can be seen that the rotatable hub 356 makes it possible to rotate the outer sheath with respect to the catheter while at the same time it is possible to extend and retract the outer sheath with respect to a device positioned within the catheter. That makes it possible to deploy the distal extremity of the device a predetermined amount without the necessity of advancing or retracting the proximal extremity of the device.

Another embodiment of the apparatus of the present invention is the apparatus 401 shown in FIGS. 19 and 20 and corresponds to the apparatus 21 shown in FIG. 1 and which includes a catheter 402 and an outer sheath 23 which is like the outer sheath 23 used in the apparatus 21. Apparatus 401 is provided with lumen portions 66a and 66b of the type hereinbefore described. The catheter 402 differs from the catheter 22 in that it has a distal extremity 403 which is provided with an extension 406 formed integral therewith which is of reduced diameter and which carries a cannula tip 407. The catheter 402 is provided with multiple lumens as for example three lumens 411, 412 and 413. The flexible elongate member 414 forming the catheter 402 is provided with a proximal portion 416 and a distal portion 417 and a transition portion 418 as well the as extension 406 and the cannula tip 407 hereinbefore described. The proximal section 416 and the distal section 417 are constructed from a multiple lumen tubing as for example triple-lumen tubing with preferably the lumens having an inside diameter of 0.017" with the lumens 411, 412 and 413 extending into a region adjacent the transition section 418. At the transition section 418, the three lumens 411, 412 and 413 terminate into a single tapered lumen 419 and thence into a single lumen 421 provided in the extension 406 and in the cannula tip 407. This lumen 421 is sized so that it will only receive one of the devices provided in any one of the lumens 411, 412 and 413 in the same manner as in the apparatus 21 hereinbefore described. As shown in FIG. 19 of the drawings, the outside diameter of the extension 406 must be slightly less than the inside diameter of the lumen 60b in the outer sheath 23, preferably for example a diameter of 0.022" to 0.025".

The cannula tip 407 is formed of a suitable metal such as stainless steel, Nitinol or platinum-iridium and preferably platinum-iridium because of its radiopacity characteristics. The cannula tip 407 preferably has approximately the same outside diameter as the outside diameter of the extension 406 and is provided with a lumen 422 which is in registration with the lumen 421. The extension 406 can have a suitable length as for example 20 cm whereas the cannula tip 407 can have a length ranging from 2–3 cm. The cannula tip 407 is provided with a bevel 424 to provide a sharp point. As can be appreciated, the outer diameter of the cannula tip 407 must be smaller than the inner diameter of the distal portion of the outer sheath 23. Suitable means is provided for forming a firm connection between the cannula tip and the extension 406 to ensure that the cannula tip 407 is not accidentally dislodged from the extension 406 during use of the same in a medical procedure. One example of such a connection is shown in FIG. 21. As shown therein, a plurality of spaced-apart annular recesses 426 are provided on the tip 407 over which the distal extremity of the extension 406 extends. Additionally suitable means such as an adhesive can be utilized to assure adherence.

A detent mechanism such as that described and shown in FIGS. 17 and 18 can be utilized in conjunction with the apparatus 401. When the detent mechanism is in a forward position as for example as shown in FIG. 17, the outer sheath is in a locked position and ensures that the cannula tip will be within the outer sheath during insertion of the catheter 402 in the vessel. As soon as the catheter is in an appropriate position in the vessel, the detent mechanism can be unlocked by depressing the tab 362 and the outer sheath 23 slid proximally permitting the beveled cannula tip 407 and the device carried thereby as for example an ultrasonic probe 26 to extend beyond the distal extremity of the outer sheath and permitting the beveled sharp tip 407 of the catheter to be advanced into a stenosis as hereinbefore described to aid in penetration of the stenosis while at the same time providing additional support for the distal extremity of the ultrasonic probe or device 26. It can be readily appreciated that when desired, the cannula tip 407 and the device 26 carried thereby can be readily brought back into the outer sheath 23 by advancing the detent mechanism 361 distally until the slider drops into the recess 352 under the force of the spring 371.

Thus it can be seen that in the embodiment shown in FIGS. 19 and 20 it is possible to provide additional means at the disposal of the physician for making it possible to penetrate particularly tough lesions by the use of the sharpened cannula tip 407 which at the same time will also provide additional rigidity to the device extending therethrough. It should be appreciated that the cannula tip 407 can be moved independently of the probe or wire 26 to create a path through which the probe or wire can be advanced.

Figure 22:
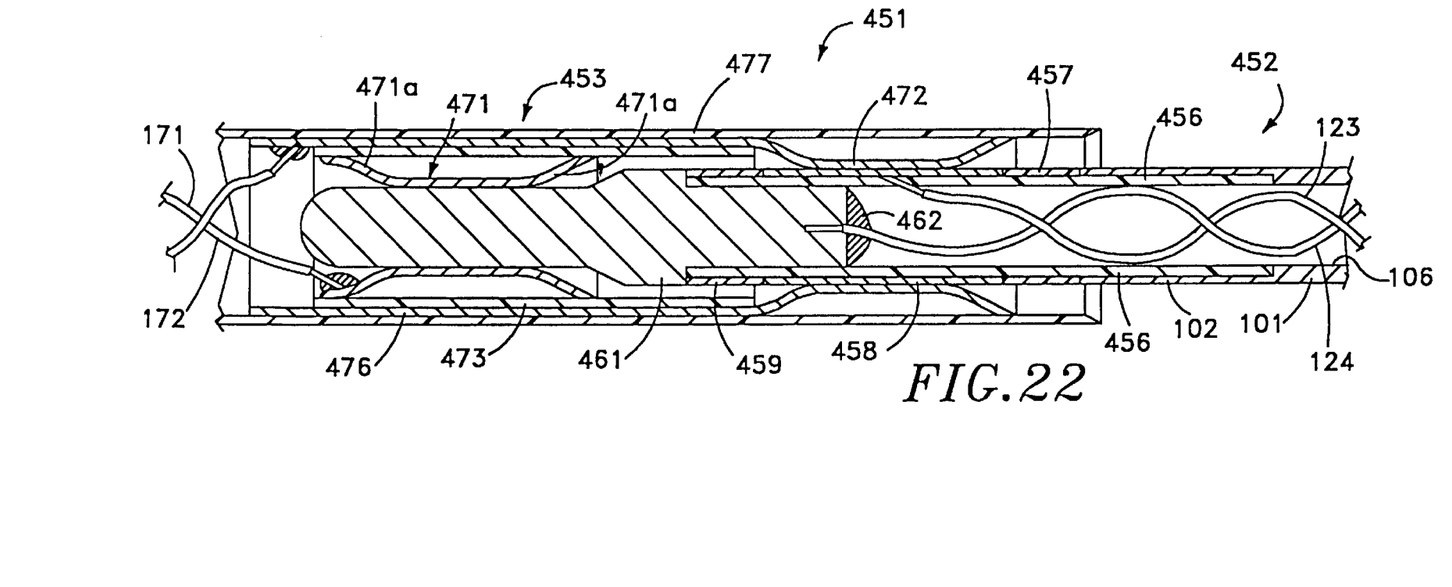
FIG. 22 is a cross-sectional view showing another embodiment of a connector utilized in the apparatus shown in FIG. 1.

Another embodiment of a connector assembly which can be utilized for the connector assembly 146 hereinbefore described is the connector assembly 451 shown in FIG. 22. It is provided with a male part 452 and a mating female part 453 which make it possible to utilize circular spring contacts rather than semi-circular spring contacts of the type as shown in the embodiment disclosed in FIG. 5. Thus the proximal extremity 102 of the flexible elongate member 101 can be formed of a hypotube as for example stainless steel or Nitinol in the male part 452. A sleeve 456 of a suitable insulating material such as a polyimide is fitted within the proximal extremity in the manner shown as for example by use of a slip fit and by the addition of adhesive if necessary. An insulating sleeve or ring 457 is mounted on the sleeve 456 just proximal of the termination of the proximal extremity 102 of the flexible elongate member 101. A conductive sleeve 458 formed of a suitable material such as silver is mounted on the sleeve 451 immediately adjacent the insulating ring 457 and the insulated conductor 123 is connected thereto as shown in FIG. 21. A retaining ring 459 is provided on the sleeve 456 for retaining the conductive sleeve 458 in place. A contact pin 461 is mounted in the insulating sleeve 456 and the other lead 124 is secured thereto as shown by solder 462. The contact pin 461 is formed of a suitable conductive material such as beryllium copper.

The female part 453 is provided with spring members for engaging the contact pin 461 and the sleeve 458 and consists of first and second cylindrical spring contacts formed of a suitable material such as beryllium copper which are mounted in a spaced apart position so that they are adapted to respectively engage the contact pin 461 and the sleeve 458. The cylindrical spring contact 471 is connected to the conductor 172 and is mounted within an insulating sleeve 473. The cylindrical spring contact 471 is provided with outwardly flared portions 471a on opposite ends of the same so as to accommodate entry of the pin 461 therein. A conductive sleeve 476 is mounted on the insulating sleeve 473 and is connected to the conductor 171 as shown. This conductive sleeve 476 is formed integral with the cylindrical spring contact 472 which is adapted to engage the conductive sleeve 458. An insulating sleeve 477 surrounds the conductive sleeve 476. Thus it can be seen that there has been provided another embodiment of a connector assembly which permits rotation of the male and female parts 452 and 453 with respect to each other while still maintaining electrical contact.

Figure 23:
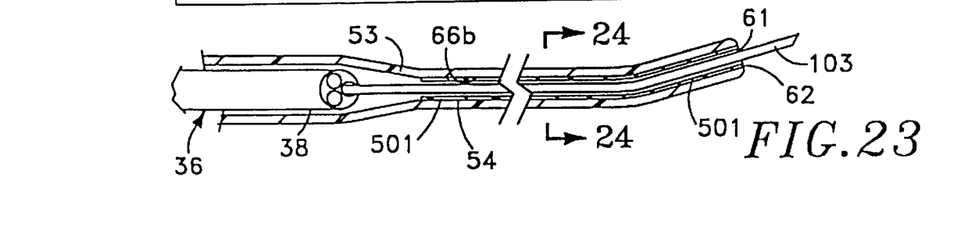
FIG. 23 is an enlarged side elevational view in cross sections of the distal extremity of a catheter and an outer sheath similar to that shown in FIG. 1 incorporating another embodiment of the present invention.

Another embodiment of an outer sheath 23 of the apparatus shown in FIG. 1 is shown in FIGS. 23 and 24 in which a liner 501 has been provided in the distal portion 54 to reduce the friction within the distal extremity 54 of the outer sheath 23. Thus there is provided a lumen 66b of a reduced size. The liner 501 is formed of a suitable friction reducing material such as Teflon™ or polyethylene and can have a wall thickness ranging from 0.0025" to 0.01" and preferably approximately 0.0003". Such a distal extremity can be provided by extruding the distal extremity 54 over a Teflon™ or polyethylene liner 501 to ensure that there is good adhesion between the liner 501 and the distal extremity which as hereinbefore explained can have a braid incorporated therein. It has been found that the use of this liner 501 is particularly efficacious in reducing friction in the lumen 66b in the distal portion 54. By making this liner 501 very thin, this liner does not unduly affect the flexibility of the distal extremity 54.

Figure 25:
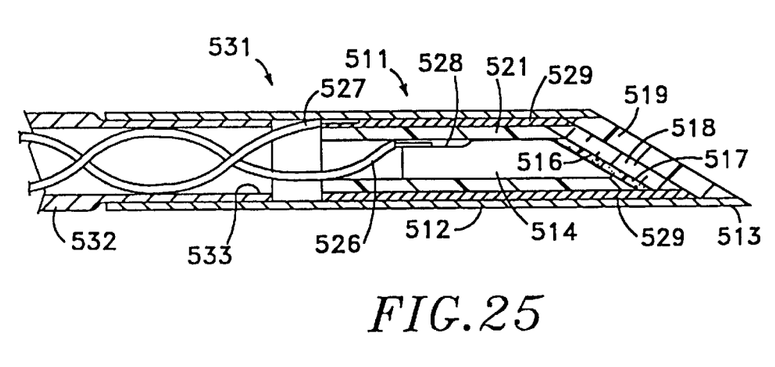
FIG. 25 is an enlarged sectional view of the distal extremity of another embodiment of the catheter shown in FIGS. 1 and 5.

Another embodiment of an ultrasonic probe incorporating the present invention is shown in FIG. 25 in which a distal extremity 511 is provided incorporating another embodiment of the invention. The distal extremity includes a metal tube 512 formed of a suitable material such as stainless steel which is provided with a beveled tip 513 having a bevel of the type hereinbefore described. A solid metal rod 514 formed of a suitable conductive material such as silver, gold, platinum, stainless steel or brass is mounted within the metal tube 512 the solid metal rod is provided with a beveled surface 516. A conductive epoxy layer 517 is provided on the surface 516 and has adhered thereto the back side or inner surface of an ultrasonic transducer 518 of the type hereinbefore described. The outer surface or front side of the transducer 518 is recessed within the beveled tip 513 to provide space for an acoustic matching layer 519 overlying the outer surface of the transducer 518. An insulating sleeve 521 formed of a suitable insulating material is disposed within the metal tube 512 and serves to insulate the metal rod 514 from the metal tube 512. Means is provided for making electrical contact with the front and back sides of the transducer 518 and consists of insulated electrical conductors 526 and 537 which extend from the distal extremity with insulated conductor 526 being soldered to a flat 528 provided on the rod 514 to make electrical contact with the back side of the transducer 518 and in which conductor 527 is soldered to a conductive layer 529 of a suitable material such as a sputtered gold layer of approximately 2 microns in thickness provided on the outer surface of insulating sleeve 521 and making electrical contact with the front side of the transducer 518 as shown.

The distal extremity 511 hereinbefore described is mounted on and forms a part of a flexible elongate member 531 which includes a tubular member 532 typically termed a hypotube formed of a suitable material such as a nickel-titanium alloy. This tubular member 532 is provided with a lumen 533 which carries the conductors 526 and 527 which extend to the proximal extremity (not shown) of the flexible elongate member 531 to be connected to a power supply in the manner hereinbefore described. The procedure to assemble them is the same as for the other embodiments. In addition, the solid metal rod provides a more solid and stable backing for the transducer to provide an improved acoustic performance for the tip and thereby providing a higher quality image.

Figure 26:
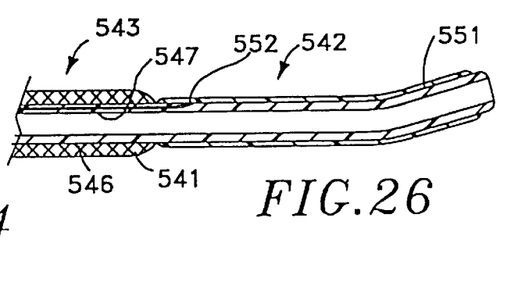
FIGS. 26 and 27 are enlarged sectional views of the distal extremity of a catheter incorporating another embodiment of the present invention showing a balloon in deflated and inflated positions, respectively.
Figure 27:
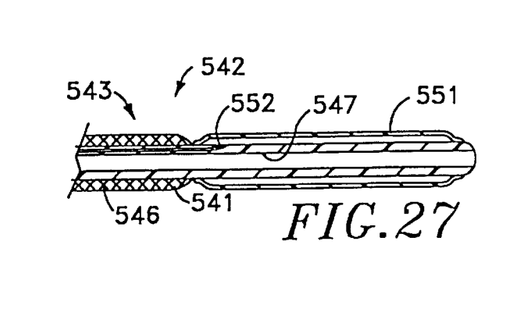

Still another embodiment of the present invention is shown in FIGS. 26 and 27 in which there has been provided a flexible elongate member 541 which has a distal extremity 542 of an outer sheath 543. The flexible elongate member 541 is formed in a manner hereinbefore described and can be in the form of a tubular member formed of plastic and having an annular braid 546 formed in the outer surface thereof and having an interior lumen 547 formed therein and extending through the distal extremity as shown. An inflatable balloon 551 is mounted on the distal extremity 542 beyond where the braid 546 terminates and is formed of a suitable non-elastic material such as PTFE or polyethylene and having a wall thickness in a range from 0.0003" to 0.001" and preferably approximately 0.0005". In a manner well known to those skilled in the art, the balloon 551 can be formed integral with the flexible elongate tubular member 541 or alternatively can be formed as a separate balloon and having the proximal and distal extremities adhered thereto by a suitable means such as an adhesive. An annular balloon inflation lumen 552 is provided for inflating and deflating the balloon 551. As shown, the tip of the flexible elongate member 541 is rounded as shown to provide an atraumatic tip.

Typically, the balloon 551 is sized so that when inflated as shown in FIG. 27, it has a size corresponding to the diameter of the distal extremity 542 where the braid 546 is present. Thus as shown, the braid 546 is eliminated at the most distal portion and the flexible elongate tubular member 541 necks down to receive the balloon 551. Thus by way of example, the balloon can have a deflated diameter of 1.7 french or approximately 0.021" and an inflated diameter of 2½ French or 0.032". The balloon 551 can have a suitable length as for example 0.150" to 5" and preferably 0.150" to 1.5". As shown, the distal extremity 542 is typically provided with a predetermined bend which the deflated balloon follows. However, when the balloon is inflated by supplying inflation fluid to the inflation lumen 552, the balloon causes straightening of the distal extremity as shown in FIG. 27 with the amount of straightening being determined by the pressure utilized to inflate the balloon. Thus it can be seen that by controlling the pressure in the balloon 551 it is possible to control the amount of straightening with the straightening ranging from the curved configuration shown in FIG. 26 and a straight condition as shown in FIG. 27.

The provision of such a balloon on the distal extremity of the flexible elongate member 541 makes it possible to negotiate difficult and complex lesions occurring in the vessels being negotiated. Because the balloon has a very low profile when deflated it can be advanced over the ultrasound guidewire 26 into a difficult region at which time if desired, the balloon can be partially inflated to cause a predilation of the lesion. At the same time, the inflation of the balloon causes straightening of the distal extremity thereby to facilitate advancement through a complex lesion. Thus by way of example by utilizing a guidewire of the present invention and having a diameter such as for example 0.014", it is possible to advance the outer sheath over this guidewire and then after the sheath is in place, the guidewire can be exchanged for a normal floppy guidewire.

It should be appreciated that rather than having a coaxial lumen for inflating the balloon as hereinbefore described, a separate lumen can be provided within the flexible elongate member 541 which can be extruded therein, as for example a flexible elongate member having a 0.003" lumen extending the length thereof. Thus it can be seen by providing a balloon on the distal extremity of the outer sheath it is possible to provide for coarse steering.

As hereinbefore explained, the balloon inflation lumen which can be identified as a secondary lumen can be placed either as a single lumen within the braided tubing or alternatively can be in the form of a coaxial lumen extending the length of the flexible elongate member.

Another embodiment of a catheter incorporating the present invention which provides increased pushability is shown in FIGS. 28 through 31. The catheter 601 shown therein consists of a flexible elongate tubular sheath, 602 having proximal and distal extremities 603 and 604. This outer sheath 602 is formed in a manner similar to that hereinbefore described for other sheaths. It is formed of 70 durometer Pebax™ and has incorporated therein a braid of a suitable type such as a braid having a thickness of 0.005" and a width of 0.025" with a pitch of 70 picks per inch to provide a sheath which has an outside diameter of about 5 French corresponding to 0.065". The sheath 602 is provided with a lumen 606 extending from the proximal extremity 603 to the distal extremity 64. The lumen 606 has a diameter of 0.052".

Figure 28:
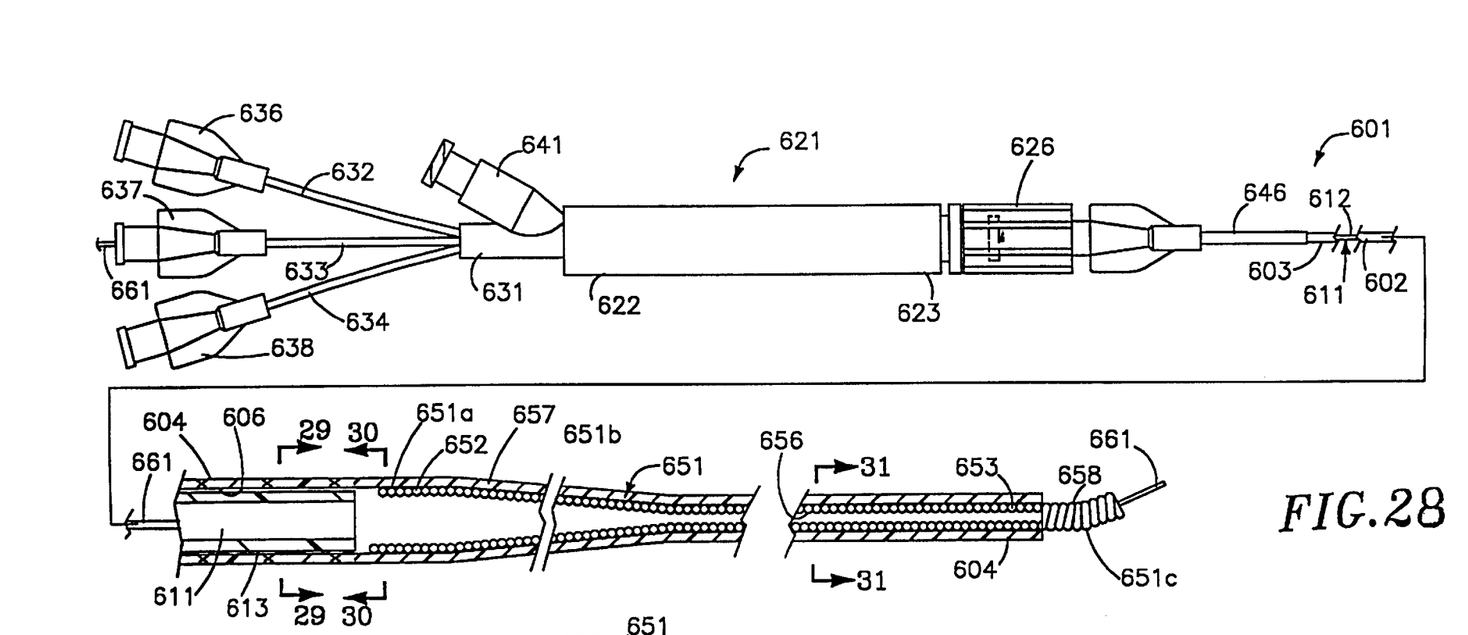
FIG. 28 is a side elevational view of another embodiment of a catheter sheath incorporating the present invention.
Figure 29:
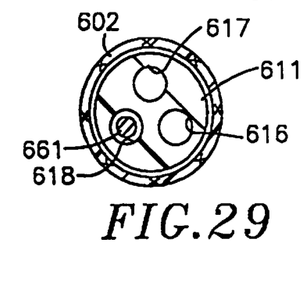
FIGS. 29, 30, and 31 are cross sectional views taken along the lines 29—29, 30—30 and 31—31, respectively.
Figure 30:
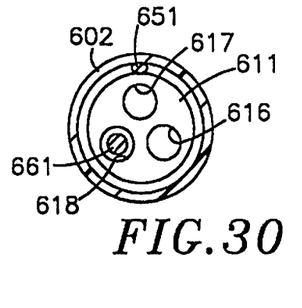
Figure 31:
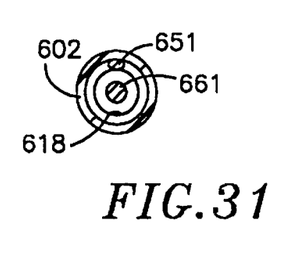

A triple lumen catheter 611 is slidably mounted in the lumen 606 of the sheath 602 and is provided with proximal and distal extremities 612 and 613. The catheter 611 is provided with three lumens, 616, 617, and 618 which extend from the proximal extremity 612 to the distal extremity 613. Each of these lumens has an inside diameter of 0.0185" and the catheter 611 has an outside diameter ranging from 0.047" to 0.049" so that it can be slidably mounted in the 0.052" lumen of the sheath 602. Thus a triple lumen catheter 611 can be rotated within the lumen 606 of the sheath 602. A handle 621 of a size that is adapted to be grasped by the human hand is provided. The handle 621 can be formed of a suitable material such as plastic and has proximal and distal extremities 622 and 623. A fitting 626 of a conventional type forming a liquid-tight seal is rotatably mounted on the distal extremity 623 of the handle 621 and has extending therethrough the proximal extremity of the triple lumen catheter 611 which extends into another fitting 631 mounted on the proximal extremity 622 of the handle 621 in a fixed and non-rotatable position.

First, second and third tubular members 632, 633 and 634 are mounted in the fitting 631 and are coupled respectively to the lumens 616, 617, and 618 in the triple lumen catheter 611. Luer-type fittings 636, 637 and 638 are secured to the tubular members 632, 633 and 634 and are in communication with the lumens within the inner tubular members 632, 633 and 634. A side port 641 is provided on the fitting 631 and is in communication with the annular space between the triple lumen catheter 611 and the wall of the sheath 602 forming the lumen 606 so that liquids, for example a radiopaque contrast liquid, can be delivered through the sheath 602 to the distal extremity of the sheath.

The proximal extremity 603 of the flexible elongate tubular sheath 602 is mounted in the fitting 626 in a fixed position so that it rotates with the fitting 626 when it is rotated. The triple lumen catheter 611 extends into the proximal extremity 603 of the sheath 602 is also secured within the fitting 626. A strain relief tube 646 is secured to the fitting and extends over the sheath 602 for a suitable distance as for example approximately 2".

A tapered coil 651 is secured to the distal extremity 604 of the sheath 602. The tapered coil 651 is formed of a suitable material such as stainless steel wire having a diameter ranging from 0.003" to 0.005" and preferably approximately 0.003" that is wound in a very tight pitch so that there is very little space between turns of the coil. The tapered coil 651 is provided with a proximal extremity 652 and a distal portion 653. Such a tapered coil 651 typically may have three portions 651a, 651b and 651c in which the intermediate portion 651b is the tapered portion and the portions 651a and 651c on opposite ends are cylindrical in shape. The coil 651 can be formed by winding wire such as of a diameter of 0.003" onto a mandrel (not shown) with the desired configuration for the coil. The tapered coil 651 is provided with a lumen 656 extending therethrough and has the proximal portion 651a with the lumen 656 therein open to all three of the lumens 616, 617 and 618 on the triple lumen catheter 611. The lumen 656 is sized so that a conventional guidewire can be extended therethrough as, for example, a guidewire having a diameter 0.014" or less. Thus the lumen 656 should have a diameter of 0.018". A Pebax™ material of a suitable durometer ranging from forty to seventy is formed as a layer 657 over the tapered coil 651 and forms a bond with the distal extremity 604 of the braided sheath 602 and extends substantially over the entire length of the tapered coil 651 but leaving only a small distal tip 658 exposed. This exposed tip 658 can be of a suitable length, as for example, ranging from 0.010" to one cm. This exposed distal tip can be provided with a preformed bend as shown of the type conventionally placed on the tip of a guidewire. It should be appreciated that if desired, the layer 657 can extend over the exposed distal tip 658. In place of the Pebax layer, shrink tubing (not shown) made from any suitable material such as PET can be provided over the tapered coil 651.

The tapered coil 651 can have a length ranging from 5" to 30" but preferably should have a length ranging from 10" to 20". The tapered portion 651b typically can have a length ranging from 1" to 11" and preferably ranging from 4" to 8". The distal portion 651c of a smaller diameter can have a length ranging from 1" to 10" and the larger diameter cylindrical portion 651a can have a length ranging from 1" to 10".

With the tapered coil 651 being formed of 0.003" wound wire, the portion 651a of the coil can have an outside diameter of 0.041" and an inside diameter of 0.0350". The layer 657 can have a suitable thickness, as for example 0.0035", to provide an outside diameter for the plastic covered tapered coil of a 0.048" to thereby closely approximate the 5 French diameter(0.065") of the sheath 602 so that a bond can be really formed between the plastic of the layer 57 and plastic of the sheath 602. In the intermediate portion 651b, there is a transition from the larger diameter portion 651a to the smaller diameter portion 651c so that the lumen 656 in the portion 651c is of a smaller diameter, as for example 0.018"±0.003". The outside diameter of the coil can be 0.024" and the outside diameter of the covering layer 657 would be 0.031".

The catheter assembly 601 shown in FIGS. 28–31 has increased pushability over the catheter assembly hereinbefore described. Instead of providing a braided flexible elongate member for the sheath 602 extending its entire length, a tapered coil 651 is provided which has a very substantially reduced diameter over that of a braided sheath extending the entire length. Since the turns of the coil 651 are immediately adjacent to each other, the coil 651 provides additional column strength for the sheath.

Increased radiopacity of the distal extremity of the catheter assembly 601 is provided because the coil 651 is itself more radiopaque and visible fluoroscopically than the braided sheath hereinbefore described.

A guidewire 661 is disposed in the Luer-type fitting 637 and in the tubular member 633 and extends through the lumen 618 of the triple lumen catheter 611 and enters into the tapered lumen 656 provided within the tapered portion 651c of the coil 651 and out through the distal extremity as shown in FIG. 28.

Another advantage of the construction shown in FIGS. 28–31 is that the guidewire friction is reduced when passing a guidewire such as guidewire 661 through the catheter assembly 601, principally because in the portion of the sheath comprised of the tapered coil 651, there is less surface contact between the guidewire and the exposed turns of the inner surfaces of tapered coil 651 to provide reduced surface area frictional contact as the guidewire is advanced through the tapered coil 651.

The catheter assembly of the present invention shown in FIGS. 28–31 because of its greatly increased pushability and its reduced overall diameter at the distal extremity makes it possible to penetrate a complex or difficult lesion with ease. The increased pushability can be quantified by ascertaining the increased column strength.

As hereinafter explained, other therapeutic devices can be introduced through the catheter assembly 601 because of the two additional lumens which are available in the triple lumen catheter 611. In utilizing an ultrasonic imaging guidewire, it is possible to rotate the imaging guidewire within the catheter assembly 601. By utilizing such an imaging guidewire it is possible to ascertain the direction in which the distal extremity of the catheter assembly 601 should be advanced to penetrate a complex lesion in a vessel.

In summary it can be seen that by utilizing closely spaced turns for the tapered coil for the distal extremity of the sheath, it is possible to provide greater pushability while at the same time providing a smaller profile at the distal tip for easier penetration into the complex lesion or atheroma. In addition, there is increased radiopacity, reduced friction and increased flexibility.

From the foregoing it can be seen that the multi-lumen catheter utilized in the apparatus of the present invention permits a physician to switch from a diagnostic imaging probe to a floppy guidewire to a stiff guidewire and then to one or more therapeutic devices without losing the position of the tip of the guidewire. There is no necessity for the physician to remove the entire guidewire from the catheter. This therefore permits the physician to switch back and forth between two different guidewires or between a diagnostic probe and a therapeutic probe carried by the multi-lumen catheter. It is possible to maintain the position of the guidewire through a tortuous path. In addition, the apparatus makes it possible to torque the distal tip of the sheath without rotation of the multi-lumen catheter and thereby avoiding entanglement of the ultrasonic probe and the guidewires.

What is claimed:

1. A method of navigating and advancing a guidewire through an occlusion in a blood vessel utilizing an apparatus including an outer sheath having a lumen therein, a catheter rotatably disposed in the lumen of the outer sheath, the catheter having at least one lumen therein, a forward looking ultrasound imaging guidewire deployable within the catheter lumen and extendable beyond the distal end of the catheter and the outer sheath, said guidewire further including a sharpened beveled tip at the distal end thereof and an ultrasonic imaging transducer mounted adjacent to the distal end of the guidewire, the method comprising advancing the distal end of the outer sheath through the vessel into proximity of the occlusion, advancing the guidewire beyond the distal end of the outer sheath and obtaining a forward looking ultrasonic image of the occlusion and the vessel, and advancing the sharpened beveled tip into the occlusion with the guidewire, with the sharpened beveled tip being utilized to facilitate steering of the guidewire while penetrating fibrous regions of the occlusion and wherein the ultrasound is utilized to provide forward looking ultrasonic imaging of the occlusion and vessel to facilitate navigation of the apparatus in the vessel.

2. The method of claim 1 wherein the outer sheath of the apparatus further includes a bend at the distal end thereof, and wherein the bend extends beyond the distal end of the catheter and wherein the sheath is rotatable independently of the catheter, and the method further comprises rotating the sheath with respect to the catheter to change the direction of the bend at the distal end thereof in order to change the direction of the guidewire.

3. The method of claim 1 wherein the apparatus further includes an angle encoder connected to the proximal end of the guidewire for generating rotational position information, and the method further comprises traversing the occlusion with the guidewire while tracking the direction of the distal end of the guidewire by utilizing the information from the angle encoder in combination with the information from the ultrasound imaging transducer.

4. A method for deploying a guidewire across a complex lesion in the vessel formed by a wall and normally having a lumen extending therethrough with the use of apparatus including a flexible elongate catheter having proximal and distal extremities and having a plurality of separate spaced apart therein extending from the proximal extremity into a location at least adjacent the distal extremity, a handle mounted on the proximal extremity of the catheter, a sheath mounted on the catheter having a proximal portion, a transition portion and a distal extremity having a lumen extending from the proximal portion through the transition portion and through the distal extremity, first and second devices at least one of which is an ultrasonic probe and at least one of which is a guidewire mounted in the plurality of separate spaced apart lumens, the lumen in the distal extremity of the sheath having a size so that it can receive only one at a time of the devices, the method comprising advancing the apparatus so that the distal extremity of the sheath is disposed in the vessel, advancing the ultrasonic probe out of the catheter and into the distal extremity of the sheath and out of the distal extremity of the sheath, supplying radio frequency energy to the ultrasonic probe and using the information gathered from the ultrasonic probe for guiding the ultrasonic probe through the vessel and into and through the complex lesion in the vessel, advancing the sheath with the ultrasonic probe through the complex lesion, withdrawing the ultrasonic probe into the catheter while retaining the distal extremity of the sheath so it extends through the lesion, advancing a selected guidewire from another lumen in the catheter and advancing it through the distal extremity of the sheath so it extends beyond the lesion, and retaining the guidewire in place while withdrawing the catheter and the sheath and thereafter performing additional medical procedures utilizing the guidewire which is in place to treat the lesion.

5. A method as in claim 3 for use with electronics including an RF generator and receiver and a computer with a display screen and a rotation encoder, comprising rotating the ultrasonic probe to obtain a cross-sectional view of the vessel being traversed and the position of the ultrasonic probe therein and rotating the rotation encoder in synchronism with rotation of the proximal extremity of the ultrasonic probe.

6. A method for advancing a guidewire through a stenosis in a body lumen by utilization of an assembly including a flexible elongate tubular member having proximal and distal extremities and a guidewire having a proximal extremity and a distal extremity slidably mounted within the flexible elongate tubular member, the distal extremity of the guidewire having a beveled sharpened tip having an exposed beveled surface, the method comprising advancing the flexible elongate tubular member in the body lumen so that the distal extremity is in the vicinity of the stenosis in the body lumen, advancing the guidewire so that the distal extremity extends beyond the distal extremity of the flexible elongate tubular member and into the stenosis and rotating the guidewire in the flexible elongate tubular member to change the angular orientation of the beveled sharpened tip of the distal extremity of the guidewire, and causing the distal extremity of the guidewire to travel in a transverse direction in the stenosis generally opposite that which the beveled surface faces.

7. A method as in claim 6 wherein an imaging transducer is carried by the distal extremity of the guidwire, the method further comprising viewing the travel of the distal extremity of the guidewire in the vessel while it is being steered by advancement and rotation of the guidewire in the lumen in the vessel.

8. A method for navigating and advancing a guidewire through a stenosis in a blood vessel utilizing an apparatus including a guidewire, an outer sheath having a lumen therein, a rotatable catheter disposed in the lumen of the outer sheath, the catheter having at least one lumen therein, an imaging guidewire having a longitudinal axis slidably mounted in the catheter and having a distal extremity and an imaging transducer carried by the distal extremity of the imaging guidewire, for viewing at an angle of 10° to 80° with respect to the longitudinal axis of the imaging guidewire, the method comprising advancing the distal end of the outer sheath through the vessel in close proximity to the stenosis, advancing the catheter in the lumen in the outer sheath so its distal extremity is disposed in the vicinity of the stenosis, advancing the guidewire through the lumen in the catheter so that the distal extremity of the guidewire extends beyond the sheath and at least to the stenosis, retracting the guidewire from the stenosis, advancing the imaging guidewire through a lumen in the catheter so that the ultrasonic transducer carried by the imaging guidewire is disposed in close proximity to the stenosis, rotating the imaging guidewire and imaging transducer to obtain an image of the vessel in the vicinity of the stenosis and utilizing the information in the image to continue advancement of the catheter within the vessel through the stenosis without penetrating the vessel wall by successive advancement of the guidewire and the imaging guidewire until the guidewire has been advanced through the occlusion.

9. The method as in claim 8 wherein the imaging guidewire of the apparatus has a sharpened distal extremity, the method further comprising advancing the sharpened tip through the stenosis, retracting the imaging guidewire in the catheter and advancing the guidewire through the stenosis in the path established by the sharpened distal extremity of the imaging guidewire.

* * * * *